(12) United States Patent
Sugimoto et al.

(10) Patent No.: US 9,791,591 B2
(45) Date of Patent: Oct. 17, 2017

(54) INSPECTION DEVICE

(71) Applicant: Ishida Co., Ltd., Kyoto (JP)

(72) Inventors: Kazuyuki Sugimoto, Ritto (JP); Takashi Kabumoto, Ritto (JP); Yuzuru Yamada, Ritto (JP)

(73) Assignee: Ishida Co., Ltd., Kyoto (JP)

( * ) Notice: Subject to any disclaimer, the term of this patent is extended or adjusted under 35 U.S.C. 154(b) by 85 days.

(21) Appl. No.: 15/022,469

(22) PCT Filed: Sep. 17, 2014

(86) PCT No.: PCT/JP2014/074593
§ 371 (c)(1),
(2) Date: Mar. 16, 2016

(87) PCT Pub. No.: WO2015/041259
PCT Pub. Date: Mar. 26, 2015

(65) Prior Publication Data
US 2016/0223705 A1 Aug. 4, 2016

(30) Foreign Application Priority Data

Sep. 18, 2013 (JP) .................................. 2013-193146

(51) Int. Cl.
*G06K 9/00* (2006.01)
*G06K 9/46* (2006.01)
(Continued)

(52) U.S. Cl.
CPC ............ *G01V 5/0016* (2013.01); *B65B 65/08* (2013.01); *G01N 23/04* (2013.01)

(58) Field of Classification Search
CPC .......... G01N 21/90; G01N 2021/9063; G01N 23/04; B07C 5/10; B07C 5/126;
(Continued)

(56) References Cited

U.S. PATENT DOCUMENTS 3,067,872 A * 12/1962 Fouse .................... B65B 57/04
209/524
9,266,625 B1 * 2/2016 Troy .................... G01N 29/265
(Continued)

FOREIGN PATENT DOCUMENTS

EP 1950527 A1 7/2008
JP H08-062030 A 3/1996
(Continued)

OTHER PUBLICATIONS

International Search Report; PCT/JP2014/074593 dated Oct. 21, 2014.
(Continued)

*Primary Examiner* — Charlotte M Baker
(74) *Attorney, Agent, or Firm* — Studebaker & Brackett PC

(57) ABSTRACT

An inspection device is provided that is capable of counting the number of contained objects of a product in which objects each having a predetermined shape are contained in a package in an overlapping manner. An inspection device 1 includes a total-number calculator 11b that estimates a total mass of a plurality of objects based on grayscale information on a transmission image and calculates the total number of objects by dividing the total mass estimated by a mass of one object.

4 Claims, 11 Drawing Sheets

(51) Int. Cl.
   *G01V 5/00*   (2006.01)
   *B65B 65/08*   (2006.01)
   *G01N 23/04*   (2006.01)

(58) Field of Classification Search
   CPC ...... B65B 57/04; B65B 65/08; G01V 5/0016; G02B 6/06
   USPC ........ 382/100, 190; 250/223 B, 206, 339.01, 250/340, 458.1, 459.1; 209/526, 653, 209/524, 531, 561, 578, 701; 356/239.4, 356/301; 235/375
   See application file for complete search history.

(56) References Cited

U.S. PATENT DOCUMENTS

2003/0053694 A1* 3/2003 Chamberlain ....... G06K 9/4604
   382/190
2012/0223130 A1* 9/2012 Knopp ............... G01N 21/3586
   235/375

FOREIGN PATENT DOCUMENTS

JP   2005-031069 A   2/2005
JP   2012-068030 A   4/2012
JP   2012-242289 A   12/2012

OTHER PUBLICATIONS

Notification of Transmittal of Translation of the International Preliminary Report on Patentability and Translation of Written Opinion of the International Searching Authority; PCT/JP2014/074593 dated Mar. 31, 2016.

O. Hirose et al.; "Stable Weight Estimation From X-Ray Image"; IEICE Technical Report; Jan. 8, 2007; pp. 205-210; vol. 106; No. 448.

The extended European search report issued by the European Patent Office dated Mar. 17, 2017, which corresponds to European Patent Application No. 14846622.0-1559 and is related to U.S. Appl. No. 15/022,469.

* cited by examiner

Fig.8

| GRAYSCALE LEVEL | ESTIMATED MASS(mg) |
|---|---|
| 0 | 1.25 |
| 1 | 1.24 |
| 2 | 1.23 |
| . | . |
| . | . |
| . | . |
| 50 | 0.5 |
| . | . |
| . | . |
| . | . |
| 219 | 0.01 |
| 220 | 0 |

INSPECTION DEVICE

TECHNICAL FIELD

The present invention relates to an inspection device that emits light to inspect the number of objects contained in package such as a bag.

BACKGROUND ART

An inspection device of this type has been widely used for inspection of cracks of objects contained in a package, inspection of any foreign substance mixed in contents, and missing part inspection of soup and filling contained in a package of, for example, an instant meal, and is used nowadays to inspect the number of contents. For example, the inspection targets of an inspection device disclosed in Patent Literature 1 are cookies, biscuits, or other items that are arranged in line and contained in a package. This inspection device extracts a region of contents in an X-ray transmission image and extracts, from this extracted region, protrusions in a direction orthogonal to a direction in which the contents are arrayed, specifically, protrusions formed on, for example, a periphery of cookies. The inspection device then counts the number of the contents based on the number of the protrusions.

An inspection device disclosed in Patent Literature 2 separates a single layer of a plurality of objects boxed in touch with each other into individual objects on an X-ray transmission image, and counts the number of contained objects based on the number of the separated objects.

CITATION LIST

Patent Literature

[Patent Literature 1] Japanese Unexamined Patent Publication No. 2012-242289
[Patent Literature 2] Japanese Unexamined Patent Publication No. 2005-031069

SUMMARY OF INVENTION

Technical Problem

However, in a case of a product in which a plurality of sausages are contained at random arrangement in a package, or a product in which a plurality of stock cubes each having an identical shape are contained randomly in a self-standing package, objects are photographed in an X-ray transmission image in an overlapping manner, so that the outline of an individual object cannot be specified. Thus, the X-ray inspection devices disclosed in the patent literatures cannot count the number of such randomly overlapping objects.

The present invention provides an inspection device capable of counting the number of contained objects of a product in which objects each having a predetermined shape are contained in a package in an overlapping manner.

Solution to Problem

An inspection device according to an aspect of the present invention emits light onto a product in which a plurality of objects each having a predetermined shape are contained, and inspects the number of the objects based on a transmission image obtained from light having transmitted through the product. The inspection device includes a total-number calculator configured to estimate a total mass of the objects based on grayscale information on the transmission image and calculate a total number of the Objects by dividing the total mass estimated by a mass of one object.

An inspection device having this configuration can estimate a total mass of objects of a product in which objects each having a predetermined shape are contained in a package in an overlapping manner, based on grayscale information on a transmission image, thereby counting the number of contained objects.

In one embodiment, the inspection device may further include a region specifier configured to specify an object region in the transmission image. When the region specifier has specified a plurality of object regions, the total-number calculator may calculate the number of the objects for each object region and sum the number of the objects calculated for each object region.

When there is variation in the mass of each object, a smaller total estimated mass as a dividend tends to lead to a higher accuracy of conversion of the number of objects. When a plurality of object regions are specified, an inspection device having this configuration calculates the number of objects for each object region and sums the number of objects for each object region, thereby achieving a higher accuracy of estimation, of the number of objects even when there is variation in the mass of each object.

In one embodiment, when having specified an object region in which at least two of the objects exist, the region specifier may separate the object region into regions for the respective objects and specify the number of the objects existing in the object region by counting the number of the regions separated.

For an object region in which at least two objects are determined to exist, processing of estimating the number of objects existing in the object region may be easier in a mass calculation by separating the object region into regions for the respective objects than in a mass estimation based on grayscale information on the region. An inspection device having this configuration allows selection of a processing method involving a smaller load on a controller when estimating the number of objects existing in an object region. This increases a processing speed of inspection of the number of objects.

In one embodiment, the inspection device may further include a storage configured to store the mass of one object. When the region specifier has specified the object region in which only one of the objects exists, the total-number calculator may estimate a mass of the objects based on grayscale information on the object region specified, and update the mass of one object stored in the storage with the mass estimated.

An inspection device having this configuration can estimates, when a transmission image includes an object region in which only one object exists, the mass of one object from the transmission image to update a mass of one object used so far with an estimated mass. This allows the mass of one object to be appropriately set even when the mass of one object varies between lots, thereby achieving an improved accuracy of calculation of the number of objects.

Advantageous Effects of Invention

The present invention can accurately calculate the number of contained objects of a product in which a plurality of objects each having a predetermined shape are contained at random arrangement in a package.

BRIEF DESCRIPTION OF DRAWINGS

FIG. 8 illustrates an exemplary conversion table.

DESCRIPTION OF EMBODIMENTS

Figure 1:
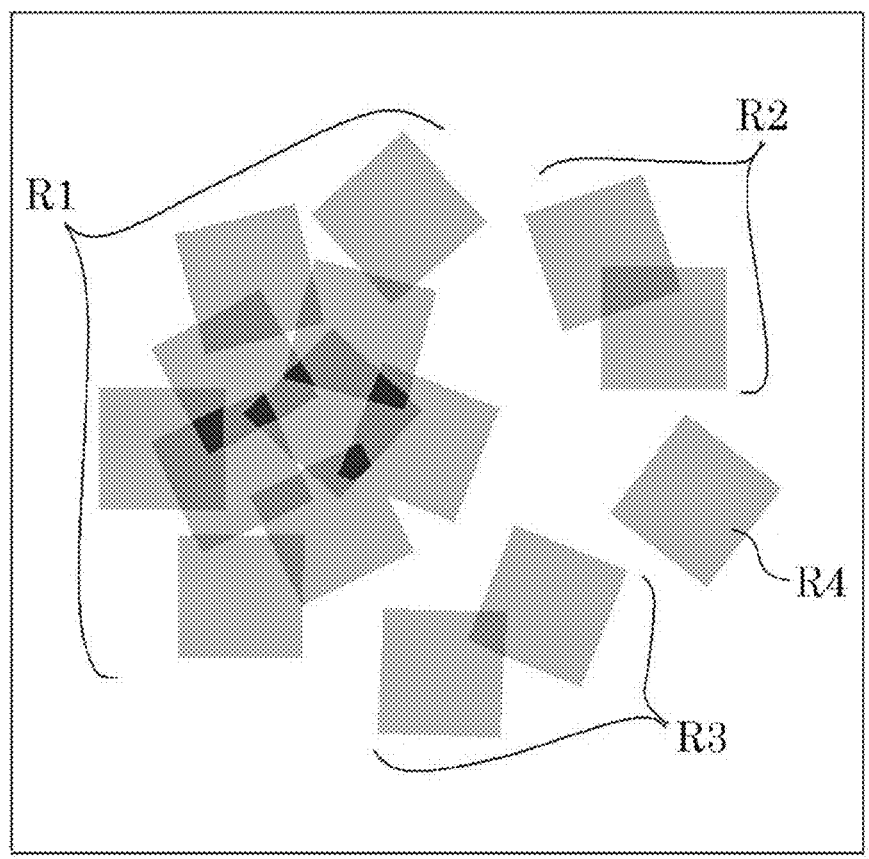
FIG. 1 illustrates an exemplary X-ray transmission image.

Embodiments of the present invention will be described below with reference to the accompanied drawings. In the drawings, any identical element is denoted by an identical reference numeral, and any duplicate description thereof is omitted. The dimension ratio of any of the drawings is not necessarily the same as that in description.

First Embodiment

Figure 6:
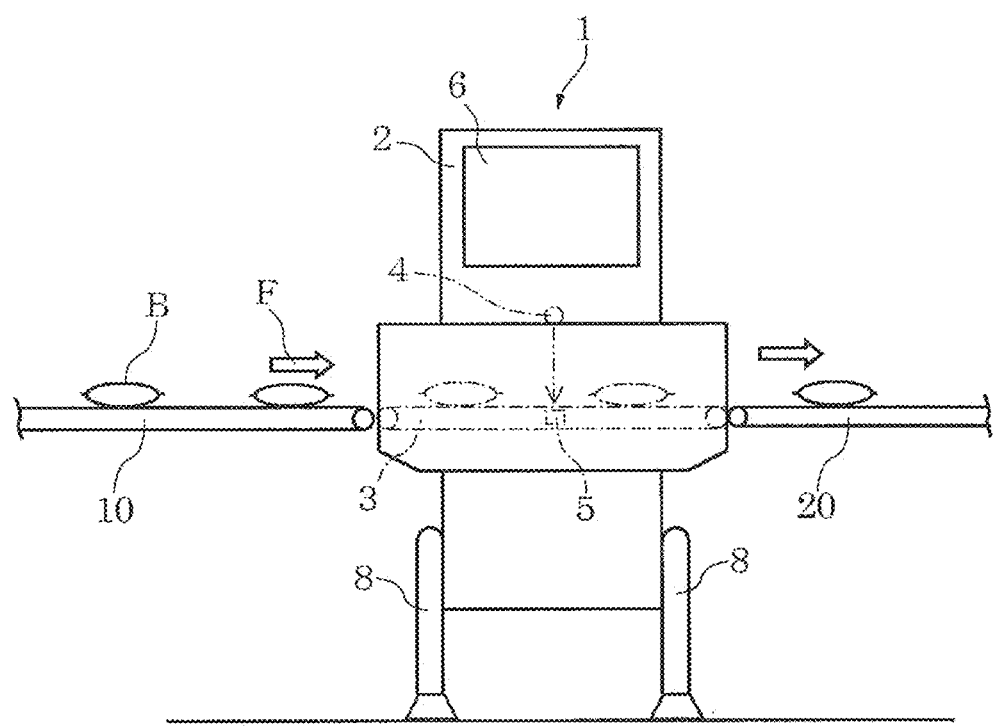
FIG. 6 is a schematic configuration diagram of an X-ray inspection device according to a first embodiment of the present invention.

FIG. 6 is a schematic configuration diagram of an X-ray inspection device (an inspection device) according to a first embodiment of the present invention. As illustrated in FIG. 6, a feed-in conveyor 10 is connected with the entrance side of this X-ray inspection device 1, and a feed-out conveyor 20 is connected with the exit side thereof. A product B conveyed from upstream is carried into the X-ray inspection device 1 by the feed-in conveyor 10. The product B is subjected to, for example, an inspection of the number of contained objects, a mixed foreign substance inspection, a missing part inspection, and a crack inspection in the X-ray inspection device 1. After various inspections at the X-ray inspection device 1, the product B is fed out to the feed-out conveyor 20. The product B thus fed out is conveyed to a packaging line through a sorting device 30 (refer to FIG. 7) downstream. Results of inspections performed at the X-ray inspection device 1 are transmitted to the sorting device 30, and then a defective product is conveyed out of the line, whereas a normal product is conveyed to the packaging line.

The X-ray inspection device 1 includes a shielding box 2 that shields an X-ray (light), a conveyor 3 bridged between the entrance and the exit of the shielding box 2, an X-ray emitter 4 that emits an X-ray onto the product B being conveyed, a line sensor 5 that detects the emitted X-ray, a touch panel 6 for setting operating and inspection conditions and inputting various setting options needed for the inspections through an operation screen, a controller 7 described later that controls these components, and support legs 8 that support the entire device including the shielding box 2.

The conveyor 3 is a belt conveyor bridged between the entrance and the exit of the shielding box 2. The conveyor 3 conveys the product B at a preset predetermined speed. A shielding curtain (not illustrated) that prevents leak of the X-ray from the shielding box 2 is provided at the entrance and the exit of the Shielding box 2.

The X-ray emitter 4 includes an X-ray tube (not illustrated) housed in the shielding box 2, and a collimator (not illustrated) that spreads an X-ray emitted from the X-ray tube like a fan in a direction orthogonal to a conveying direction F of the product B. An X-ray emitted from the X-ray emitter 4 toward the line sensor 5 transmits through the product B and the belt of the conveyor 3 and is received by the line sensor 5.

The line sensor 5 includes a plurality of photodiodes linearly arrayed in the direction orthogonal to the conveying direction F of the product B, and a plurality of scintillators placed over the photodiodes. An X-ray having transmitted through the product B is converted into light at each scintillator. The light thus converted at each scintillator is converted, into an electric signal at the corresponding photodiode and is output as an X-ray transmission signal. Each X-ray transmission signal thus output is converted into a digital quantity at an A/D converter not illustrated, and is sequentially input to a total-number calculator 11b described later.

The touch panel 6 allows, through manipulation of a setting screen displayed on its liquid crystal display as a full-dot display, start and stop of the X-ray inspection device 1, setting of necessary operating and inspection conditions, and manipulation to optimize an estimated mass, for example. An initial screen before starting an operation allows setting of, for example, the speed of the conveyor 3 and the X-ray intensity of the X-ray emitter 4. A screen after starting an operation allows, for example, a detection sensitivity at processing of an X-ray transmission image (transmission image), setting of X-ray output and dark-part enhancement for executing a mass estimating function, manipulation to optimize a correspondence relation between the grayscale level of an inspection target product and an estimated mass, setting of a true mass of one object, and setting of a planar dimension per object.

Figure 7:
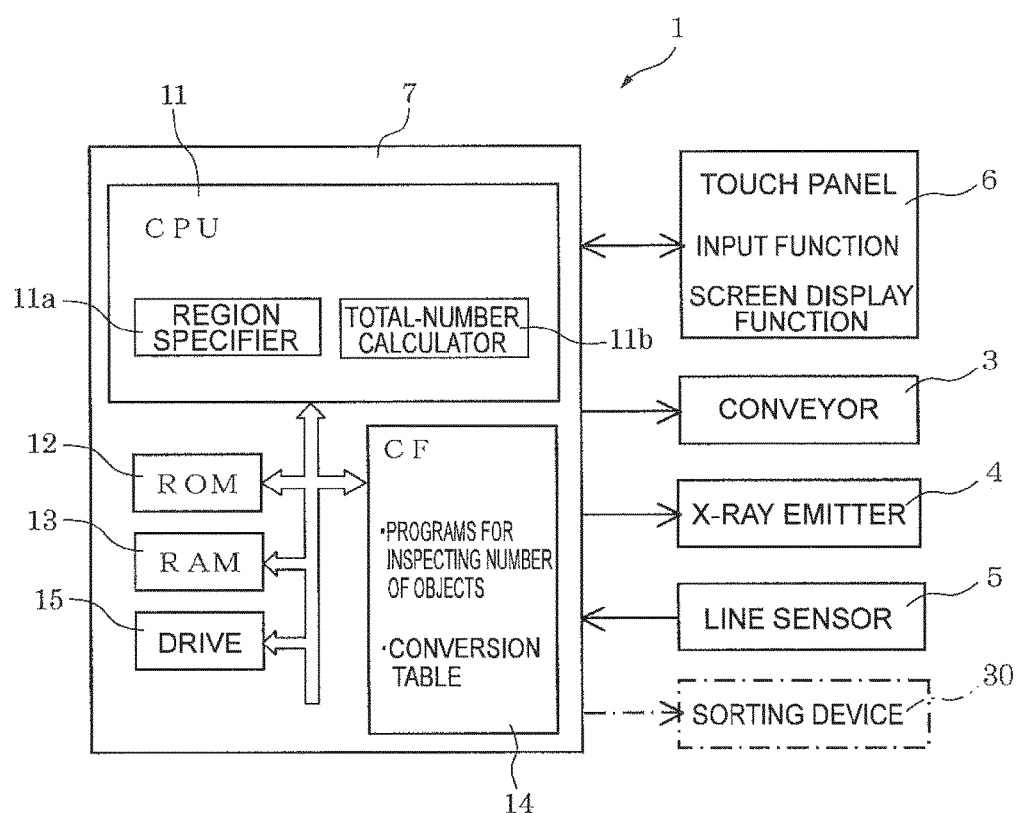
FIG. 7 is a block diagram of a functional configuration of the X-ray inspection device of FIG. 6.

The controller 7 illustrated in FIG. 7 is configured as a computer, and is connected with the conveyor 3, the X-ray emitter 4, the line sensor 5, and the touch panel 6 to control the conveyor 3, the X-ray emitter 4, the line sensor 5, and the touch panel 6. The controller 7 is also connected with the sorting device 30 and transmits an inspection result at the X-ray inspection device 1 to the sorting device 30.

The controller 7 includes a CPU 11, a ROM 12, a RAM 13, a high-capacity compact flash (CF) (registered trademark) (storage) 14, and a drive 15 for storage media. The CPU 11, the ROM 12, the RAM 13, the CF 14, and the drive 15 are mutually connected through an address bus and a data bus.

The ROM 12 stores typical inspection programs for the mixed foreign substance inspection, the missing part inspection, and the crack inspection, for example. The CF 14 stores various programs for inspecting the number of objects. The CF 14 stores therein, for example, an image processing program described later, an optimization 110 program for optimizing a conversion table illustrated in FIG. 8 based on true masses, and a mass estimation program for estimating the mass of objects using the conversion table and calculating the number of the objects from an estimated mass and a mass of one object. The CF 14 also stores the conversion table illustrated in FIG. 8, a true mass of one object, and the number of pixels occupied by one object in an X-ray transmission image.

A region specifier 11a and the total-number calculator 11b illustrated in FIG. 7 represent functions achieved by the CPU 11 executing various programs. The CPU 11 reads out various programs from the ROM 12 and/or the CF 14 and executes, for example, the mixed foreign substance inspection, the missing part inspection, and the crack inspection. These inspections are not different from those conventional, and thus their descriptions are omitted. Instead, the inspection of the number of objects performed by the region specifier 11a and the total-number calculator 11b will be described in detail.

The region specifier 11a loads the X-ray transmission signal output from the line sensor 5 onto the RAM 13 by executing the image processing program read out from the CF 14, and forms a two-dimensional X-ray transmission image. Next, the region specifier 11a provides the X-ray transmission image with mask processing to form the X-ray transmission image from which an image corresponding to a package as illustrated in FIG. 1 is removed. Subsequently, the region specifier 11a binarizes this X-ray transmission, image with a predetermined threshold to form a binary image illustrated in FIG. 2.

Figure 2:
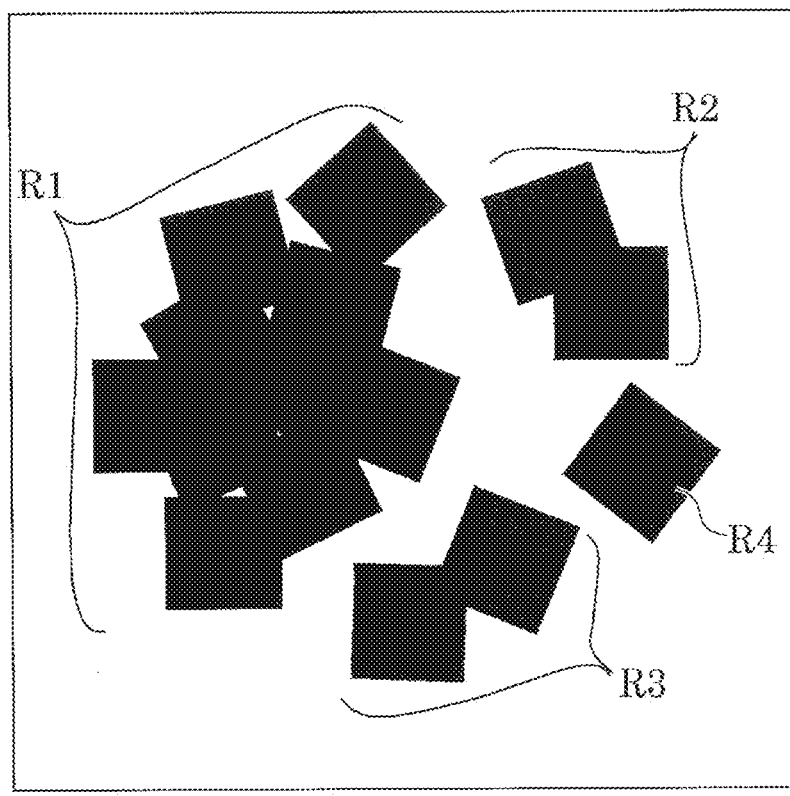
FIG. 2 is a binary image of the X-ray transmission image of FIG. 1.

The region specifier 11a provides this binary image with labeling processing to specify, as object regions, regions R1 to R4 in which objects are photographed in the X-ray transmission image as illustrated in FIG. 2. The region specifier 11a compares the number of pixels occupied by one object and the number of pixels included in each of the regions R1 to R4. In the first embodiment, the region specifier 11a specifies the region R1 as an object region in which three objects or more exist, the regions R2 and R3 as object regions in each of which two objects exist, and the region R4 as an object region in which one object exists. The number of pixels occupied by one object is calculated as the number of pixels on the X-ray transmission image based on a planar dimension input through the touch panel 6 in advance. The calculated number of pixels occupied by one object is stored in the CF 14.

Figure 4:
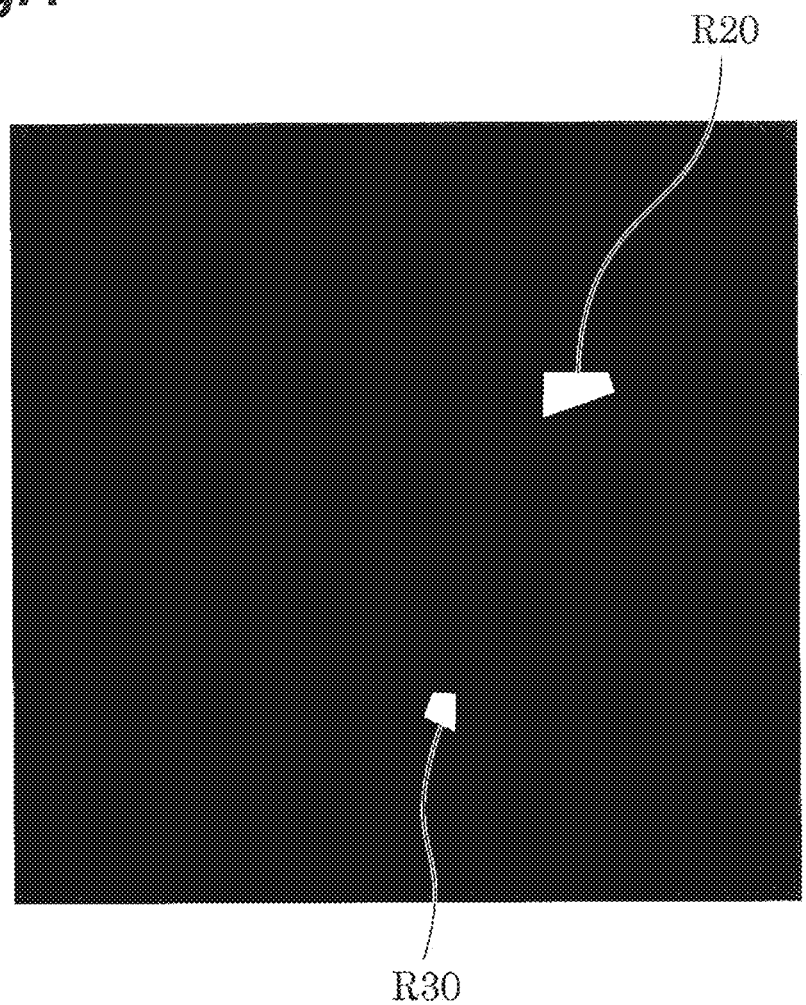
FIG. 4 is an inverted diagram of overlapping parts of objects cut out from the binary image of FIG. 3.

Subsequently, the region specifier 11a separates the regions R2 and R3 in each of which two objects exist into two object regions in each of which one object exists. In other words, the region specifier 11a separates one object region in which two objects exist into two object regions for the respective objects. Then, the region specifier 11a determines, based on the number of pixels included in a separated object region, whether a separated object region is constituted by the number of pixels occupied by one object. Specifically, a threshold of binarization of the X-ray transmission image illustrated in FIG. 1 is set to be a grayscale level lower than a grayscale level corresponding to the thickness of one object. This obtains an image of overlapping parts R20 and R30 only as illustrated in FIG. 4. FIG. 4 illustrates a black-white inverted image of the overlapping parts R20 and R30.

Figure 3:
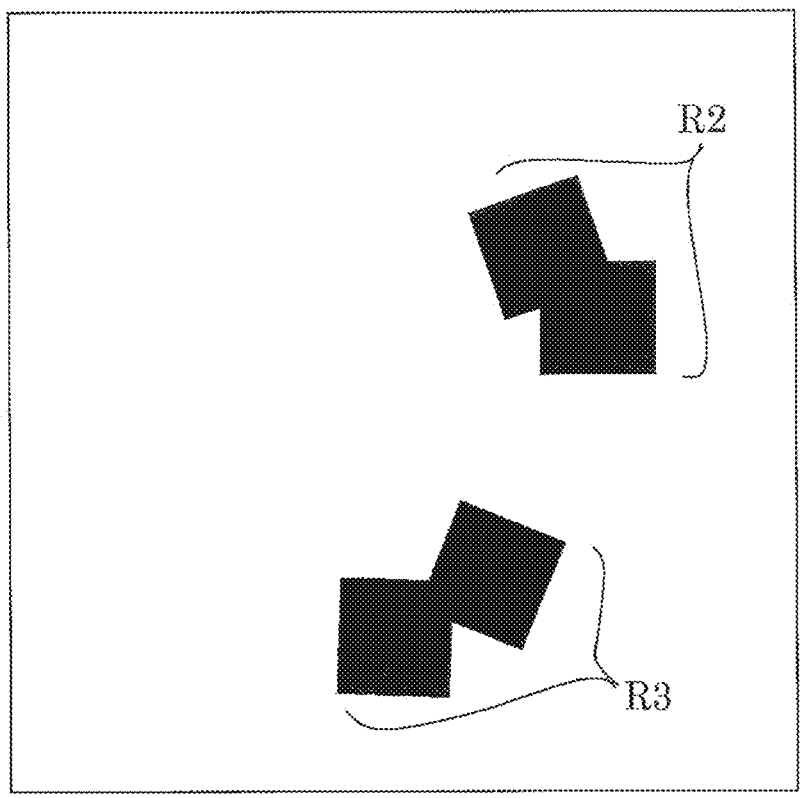
FIG. 3 illustrates regions R2 and R3 cut out from the binary image of FIG. 2.
Figure 5:
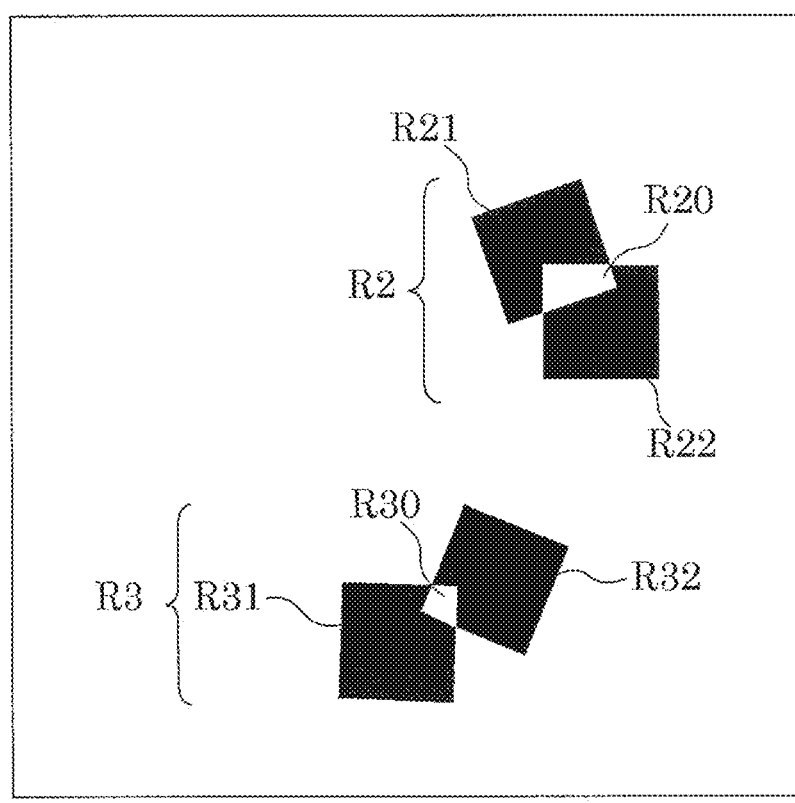
FIG. 5 is a diagram in which the overlapping parts in FIG. 4 are placed over the binary image of FIG. 3.

Next, the region specifier 11a places the black-white inverted image of the overlapping parts R20 and R30 over the binary image illustrated in FIG. 3 to form an image illustrated in FIG. 5 in which the overlapping parts R20 and R30 are removed. Subsequently, for the region R2, the region specifier 11a adds the overlapping part R20 to each of the black regions R21 and R22 occupied by two objects, and determines whether the sum of the number of pixels in the overlapping part R20 and the region R21 and the sum of the number of pixels of the overlapping part R20 and the region R22 are each equivalent to the number of pixels occupied by one object. Similarly, for the region R3, the region specifier ha adds the overlapping part R30 to each of black regions R31 and R32, and determines whether the sum of the number of pixels in the overlapping part R30 and the region R31 and the sum of the number of pixels in the overlapping part R30 and the region R32 are each equivalent to the number of pixels occupied by one object. Having determined that the number of pixels in any of the regions R2 and R3 is equivalent to the number of pixels occupied by one object, the region specifier 11a specifies that two objects exist in the region.

When this processing has ended, the CPU 11 executes the mass estimation program to bring the total-number calculator 11b into operation. The total-number calculator 11b estimates the total mass of a plurality of objects exist in the region R1 based on the grayscale information on the region R1 in the X-ray transmission image. In other words, for the region R1 in which the objects exist, the total-number calculator 11b reads out the estimated mass corresponding to the grayscale level of each pixel included in the region R1 from the conversion table illustrated in FIG. 8, and sums the estimated masses for the pixels thus read out to calculate an estimated mass of all objects exist in the region R1. Subsequently, the total-number calculator 11b divides the estimated mass thus calculated by a mass of one object, thereby calculating the total number of objects belonging to the region R1.

When each of the object regions specified by the region specifier 11a is an object region in which three objects or more exist, the total-number calculator 11b calculates an estimated mass based on the grayscale information on each object region. Next, the total-number calculator 11b divides this estimated mass by a mass of one object to calculate the number of objects existing in each object region, and then sums these numbers of objects to calculate the total number of objects (total number of objects contained in the product B). When each of the object regions specified by the region specifier 11a is an object region in which one object exists, the total-number calculator 11b calculates the total number of objects by counting the number of object regions.

A mass of one object may be a true mass measured by a mass measurer and input through the touch panel 6, or may be calculated in advance using the X-ray inspection device 1. The mass thus set varies with different manufacturing lots in some cases, and thus when an object region in which only one object exists is specified, the total-number calculator 11b may use, as the mass of one object, a mass estimated based on the grayscale information on this object region. Alternatively, if the deviation between the mass estimated from the object region in which only one object exists and a mass of one object used so far exceeds an allowable limit, the total-number calculator 11b may update the mass of one object used so far with the estimated mass newly obtained.

Figure 9:
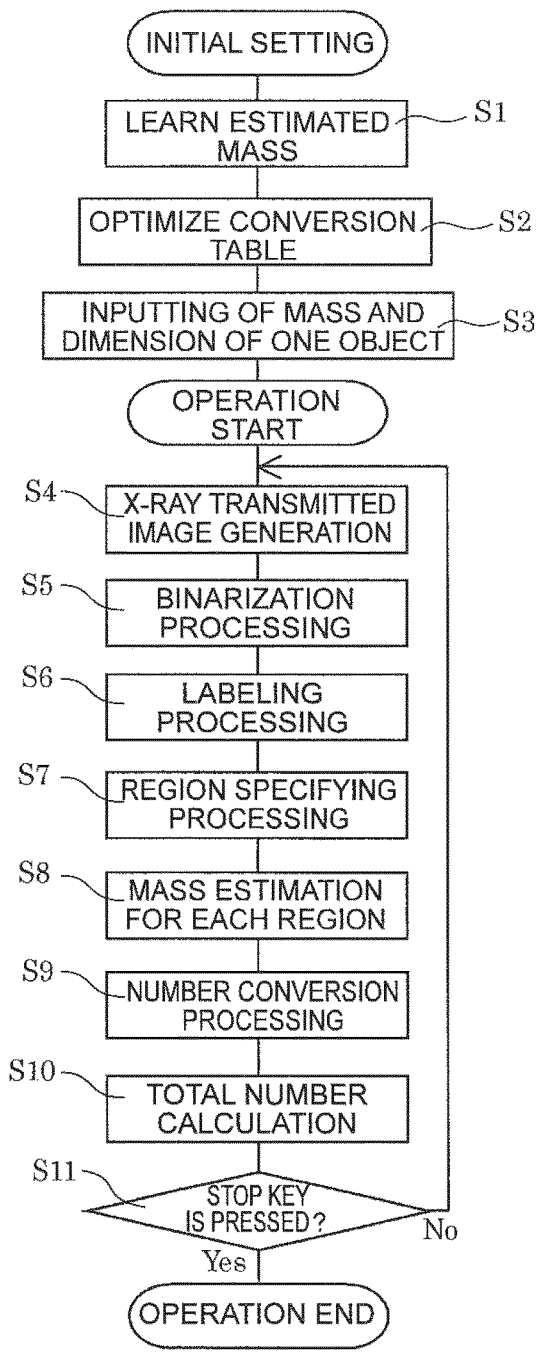
FIG. 9 is a flowchart of an exemplary operation of the X-ray inspection device of FIG. 6.

Next, the operation of the X-ray inspection device 1 according to the first embodiment is described with reference to a flowchart of FIG. 9.

In the X-ray inspection device 1, the following initial setting is performed to estimate the mass of any object contained, in the inspection target product B. In other words, a plurality of, preferably, 10 or more images of the product B are captured in the X-ray inspection device 1 to acquire the X-ray transmission images of the product B at various grayscale levels, in other words, the X-ray transmission images of objects in various states.

To operate the X-ray inspection device 1, the X-ray inspection device 1 is first switched to an estimated-mass learning mode to capture at least 10 images of the product B. Before the image capturing, the product B is fed into the conveyor 3 with different orientations and/or angles of the package so that objects contained in the package overlap each other in a complicated manner or are placed flatly. The X-ray inspection device 1 stores the X-ray transmission image at each image capturing, and these images are displayed on the touch panel 6 (step S1).

Subsequently, when the true mass (weight) of the product B is input through the touch panel 6 and a start key displayed on the touch panel 6 is pressed, the optimization program is executed. This produces a provisional conversion table using the grayscale level of each pixel included in the X-ray transmission image at each image capturing and Expression (1) described below. Next, the estimated mass of the product B is obtained based on this conversion table and the grayscale information on the X-ray transmission image captured at each capturing interval in advance. Then, for each grayscale level, the provisional conversion table is adjusted based on the deviation between the estimated mass thus obtained and the true mass, whereby optimization is performed. In this manner, when the optimization has ended, the deviation between the estimated mass and the true mass is converged substantially within several percents (step S2).

When a conversion table dedicated to the inspection target product B is finally obtained and a mass of one object (weight) and the dimension of one object are input through the touch panel 6 (step S3), the mass of one object is stored in the CF 14 and the Dumber of pixels corresponding to the dimension is calculated and simultaneously stored in the CF 14.

After this preparation is completed, the X-ray inspection device 1 is switched to a normal mode to start operating. When the conveyors 3, 10, and 20 are driven to sequentially feed each product B into the X-ray inspection device 1, each output from the line sensor 5 is sequentially input to the controller 7, so that a two-dimensional X-ray transmission image is formed on the RAM 13 and the X-ray transmission image thus formed is simultaneously displayed on the touch panel 6. When the grayscale level of the X-ray transmission image formed on the RAM 13 has largely changed, the X-ray transmission images that were captured slightly before the time of this change are loaded onto a working area. When the grayscale level stops changing after the grayscale level has largely changed, the controller 7 determines that the product B has passed through the line sensor 5, and specifies the X-ray transmission images obtained so far as processing targets (step S4). Subsequently, each X-ray transmission image specified as a processing target is subjected to mask processing, and thus a part in which the package such as a bag is photographed is removed (part in which any non-object is photographed), from the X-ray transmission image.

Next, having binarized the X-ray transmission image, the region specifier 11a performs labeling processing on the X-ray transmission image thus binarized to specify the regions R1 to R4 as illustrated in FIG. 2 in which objects are photographed (steps S5 and S6). Next, the region specifier 11a compares the number of pixels occupied by one object and the number of pixels in each of the regions R1 to R4 to specify the number of objects in each of the regions R1 to R4. In the first embodiment, the region specifier ha compares the number of pixels occupied by one object and the number of pixels in each of the regions R1 to R4, thereby specifying the region R1 as an object region in which three objects or more overlap one another, the regions R2 and R3 as object regions in each of which two objects overlap one over the other, and the region R4 as an object region in which only one object exists. Next, the region specifier 11a separates each of the regions R2 and R3 for each object belonging to the region R2 and each object belonging to the region R3. Next, the region specifier 11a compares the number of pixels in each separated image and the number of pixels occupied by one object to determine whether the number of objects in the separated image is one (step S7).

The distribution of object regions in the X-ray transmission image illustrated in FIG. 2 is an example, and arrangement and overlapping of objects differ each time. For example, the number of object regions is one when all objects contained as a product overlap one another, whereas the number of object regions is two when objects that are overlapped one another are separated into two groups.

When each of the regions R1 to R4 is specified in this manner, the total-number calculator 11b performs processing in accordance with the characteristic of each object region. In other words, for the region R1 (in which a plurality of objects are photographed), the total-number calculator 11b reads out an estimated mass corresponding to the grayscale level of each pixel belonging to the region R1 from the conversion table in FIG. 8, and calculate the total estimated mass of the region R1 by summing the estimated masses of the pixels thus read out (step S8). Next, the total-number calculator 11b divides the estimated mass thus calculated by a mass of one object to calculate the number of objects belonging to the region R1 (step S9). Next, the total-number calculator 11b adds the number of objects in the regions R2, R3, and R4 specified at step S7 to the number of objects calculated at step S9, to calculate the total number of objects contained as the product B (step S10).

When only one object region is specified, the total mass may be estimated based on the grayscale information on the specified object region and divided by a mass of one object to obtain the total number of objects contained as the product B. When the number of specified object regions is two, the number of objects may be calculated for each object region and summed to calculate the total number of objects contained as the product B. The total number of objects contained as the product B calculated in this manner is displayed on the touch panel 6 and recorded as an inspection result in the CF 14.

In the X-ray inspection device 1, this series of steps are repeated each time the product B is fed in. The X-ray inspection device 1 ends this processing when an operation stop key is pressed (step S11).

Next, exemplary region specific processing and number calculation processing in the X-ray inspection device 1 according to the first embodiment are described in detail.

FIG. 1 illustrates an exemplary X-ray transmission image for describing the present invention. FIG. 1 illustrates an image obtained by capturing a plurality of rectangular objects having an identical shape, overlapping one another. In the image in FIG. 1, part indicating the package such as a bag is removed by mask processing.

The binarization of the X-ray transmission image in FIG. 1 with the predetermined threshold provides the image illustrated in FIG. 2. Labeling processing on the binary image illustrated in FIG. 2 can extract the black regions R1 to R4 in which objects are photographed. For each of the regions R1 to R4 thus extracted, the total-number calculator 11b may estimate a mass based on the grayscale information on the corresponding one of the regions R1 to R4 in FIG. 1. Specifically, the total-number calculator 11b reads out an estimated mass corresponding to the grayscale level of each pixel in the regions R1 to R4 from, for example, the conversion table illustrated in FIG. 8, and sums the estimated masses of the pixels thus read out to calculate a total estimated mass for the regions R1 to R4. Subsequently, the total-number calculator divides the estimated mass thus calculated by a known mass of one object to calculate the total number of objects contained in the package such as a bag.

The present embodiment allows an accurate calculation of the number of objects contained in the product B in which a plurality of objects each having a predetermined shape are contained at random arrangement in a package. Thus, the present embodiment provide the X-ray inspection device 1 that is a novel X-ray inspection device capable of inspecting the number of contained objects as well as performing, for example, the mixed foreign substance inspection and the missing part inspection.

A mass of one object to be used may be a true mass measured by a mass measurer, or may be an estimated mass obtained through the mass inspection of only one object in advance by the X-ray inspection device. Alternatively, when an inspection target product is used, the mass of one object may be an estimated mass as the average of estimated masses obtained by inspecting, by the X-ray inspection device, the product whose objects are arranged evenly to avoid overlapping in a package.

The conversion table described above is obtained as follows. X-ray transmission images of an inspection target product at various grayscale levels are obtained by capturing images of the product at various angles in advance. Then, an estimated mass m corresponding to the grayscale level of each pixel in each X-ray transmission image thus obtained is calculated based on Expression (1) below, and this estimated mass (mg) is stored in a table in association with the grayscale level.

$$m = ct = -c/\mu \times ln(I/Io) = -\alpha ln(I/Io) \quad (1)$$

(where m represents the estimated mass, c represents a coefficient for converting the thickness of an object into mass, t represents the thickness of the object, I represents the brightness of the pixel when light does not transmit through the object (when no object is present), Io represents the brightness of the pixel when light transmits through the object, and μ represents a ray absorption coefficient.)

Then, the estimated mass of the object using this conversion table and the true mass thereof are compared to adjust the conversion table so that the estimated mass is equal to the true mass. The conversion table is adjusted using Japanese Patent No. 5148285 acquired by the applicant. In this manner, the conversion table for the inspection target product is prepared in advance, and a mass is calculated by converting the grayscale level of each pixel into the estimated mass.

When there is variation in the mass of each object, a smaller total estimated mass as a dividend leads to a higher accuracy of the conversion of the number of objects. Thus, the first embodiment specifies a region (object region) in the X-ray transmission image, in which any object exists. In a case in which there are two or more object regions thus specified, the total-number calculator may calculate the number of objects in each object region and sum the calculated numbers. For example, in the case of the regions R1 to R4 as separate object regions as illustrated in FIG. 1, an estimated mass for each of the regions R1 to R4 is obtained and divided by a mass of one object to calculate the number of objects in the region, and these numbers are summed to achieve a minimized error in the conversion of the number of objects.

When any object region is determined to be a region in which at least two objects exist based on the number of pixels occupied by one object, a mass calculation by separating the object region into regions for the respective objects may simplify the processing compared with that in a mass estimation based on the grayscale information on the object region. Thus, in the first embodiment, any object region in which at least two objects exist may be separated into regions for the respective objects to count the number of the separated regions. For example, the image illustrated in FIG. 3 is obtained by cutting out, from the image illustrated in FIG. 2, the regions R2 and R3 each determined to be a region in which two objects exist based on the number of pixels occupied by the object region. The binarization of this image by adjusting a threshold so that any overlapping part becomes distinct can extract the overlapping parts R20 and R30. The black-white inversion of the overlapping parts R20 and R30 provides the binary image illustrated in FIG. 4. Placing the overlapping parts R20 and R30 illustrated with white over the image illustrated in FIG. 3 provides the image illustrated in FIG. 5 from which the overlapping parts R20 and R30 are removed. Then, adding the overlapping part R20 to each of the black regions R21 and R22 in the region R2 reveals the number of pixels for the corresponding one of the two objects belonging to the region R2, and it is determined that the two objects exist in the region R2 if the number of pixels thus revealed is equivalent to the number of pixels occupied by one object. Similarly, whether two objects exist can be determined for the region R3. The total number of objects contained as the product B can be obtained by summing the number of objects thus obtained and the number of objects obtained for the other regions R1 and R4.

The mass of one object may vary between lots. In such a case, in the first embodiment, an object region in the X-ray transmission image, in which only one object is included, is specified, a mass is estimated based on the grayscale information on the object region thus specified, and a mass of one object used so far is updated with the mass thus estimated. For example, as illustrated in FIG. 2, labeling processing on a binary image can extract the regions R1 to R4 in which objects are photographed. The number of pixels occupied by one object is already known from the dimension of one object, and thus the comparison between the number of pixels occupied by one object and the number of pixels in each of the regions R1 to R4 can specify an object region including only one object. In the example of FIG. 1, the region R4 is determined to be an object region including only one object, and thus the total-number calculator 11b estimates the mass of one object based on the grayscale information on the region R4, and compares the estimated mass and a mass of one object used so fax (stored in a storage such as the CF 14), and updates the mass of one object used so far with the newly estimated mass if the deviation thereof exceeds an allowable amount.

When objects contained in one package (objects contained as one product) can be assumed to be substantially uniform, a total estimated mass may be divided by an estimated mass obtained from a region including one object. When there are a plurality of object regions in each of which only one object is included, the total estimated mass obtained based on the grayscale information on the X-ray transmission image may be divided by the average value of an estimated mass of one object obtained based on the gray scale information on each object region. In addition, a mass of one object used so far may be updated with the averaged estimated mass of one object.

Second Embodiment

The first embodiment describes the example in which the X-ray inspection device 1 is adopted as a device that emits light (electromagnetic wave) onto a product to acquire a transmission image obtained from light having transmitted through the product, but the present invention is not limited thereto. For example, a near-infrared inspection device may be adopted as a device that emits light onto a product. A near-infrared inspection device (inspection device) 101 will be described below with reference to FIGS. 10 and 11.

Figure 10:
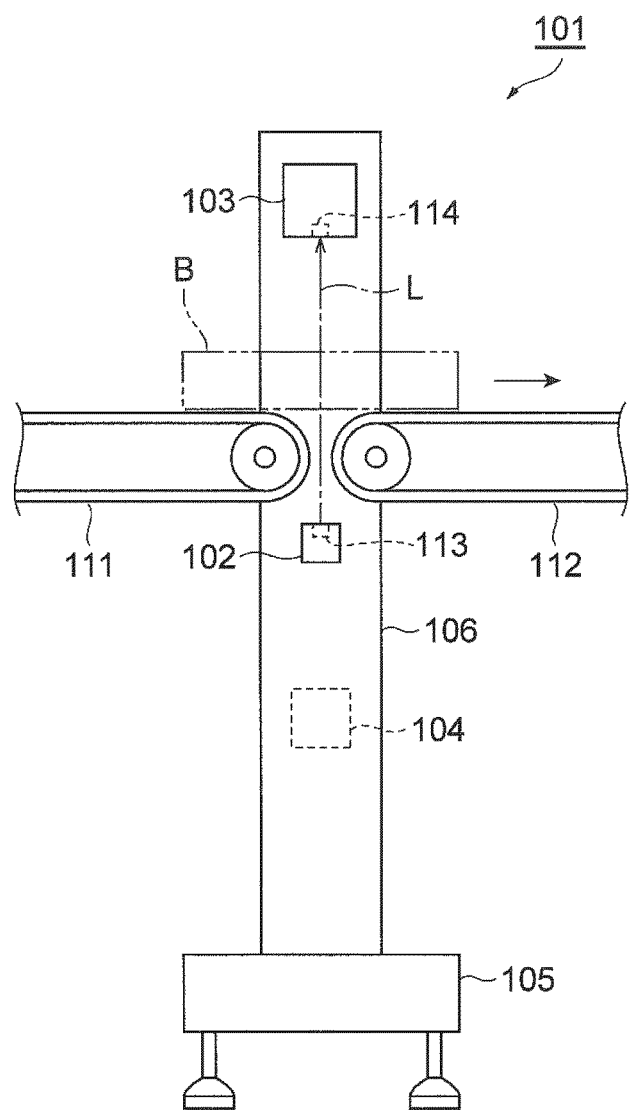
FIG. 10 is a schematic configuration diagram of a near-infrared inspection device according to a second embodiment of the present invention.

As illustrated in FIG. 10, the near-infrared inspection device 101 includes a light emitter 102, a light detector 103, and a control computer 104. The light emitter 102 is arranged below conveyors 111 and 112. The light detector 103 is arranged above the conveyors 111 and 112. The light emitter 102 and the light detector 103 face each other via a gap provided between the conveyors 111 and 112.

The near-infrared inspection device 101 handles, as inspection targets, a colorless or single color package and the product B having any object contained in the package. The package is made of a material having optical transparency such as a transparent material or a translucent material. The material of the package may have color itself, or the package may be colored by, for example, printing.

The light emitter 102 includes, below the gap between the conveyors 111 and 112, a near-infrared emitter 113 extending along the gap. When the product B conveyed by the conveyors 111 and 112 passes on the gap between the conveyors 111 and 112, the light emitter. 102 emits a near-infrared light (light) onto the product B from the near-infrared emitter 113. The near-infrared light has a wavelength of 780 nm to 1100 nm.

The light detector 103 includes, above the gap between the conveyors 111 and 112, a near-infrared line sensor 114 extending along the gap. The light detector 103 detects, through the near-infrared line sensor 114, transmitted light from the product B irradiated with the near-infrared light when the product B conveyed by the conveyors 111 and 112 passes on the gap between the conveyors 111 and 112, and outputs a detection signal.

The near-infrared line sensor 114 detects the near-infrared light having transmitted through the product B. The near-infrared line sensor 114 includes a plurality of pixels 114*a* linearly arrayed in a horizontal direction orthogonal to a conveying direction of the product B by the conveyors 111 and 112.

As illustrated in FIG. 10, the light emitter 102 and the light detector 103 are cantilever-supported by a support 106 standing on a base 105 and an optical path L of the near-infrared light from the light emitter 102 to the light detector 103 is exposed to surrounding atmosphere. That is, an inspection region of the product B is not covered by a shielding box, for example. Thus, the near-infrared inspection device 101 does not require, for example, a shielding box, so that the light emitter 102 and the light detector 103 can be cantilever-supported by the support 106. This facilitates installation of the near-infrared inspection device 101 at a desired gap between conveyors in a conveyance line including a plurality of arrayed conveyors.

The control computer 104 is housed in the support 106 and performs operation control of the near-infrared inspection device 101 and various signal processing. For example, the control computer 104 acquires a near-infrared transmission image of the product B based on the detection signal output from the light detector 103, estimates the mass of any object contained in the product B based on the grayscale information on each pixel in the near-infrared transmission image, and then divides an estimated mass by a mass of one object. The support 106 is provided with, in addition to the control computer 104, a display unit such as a display and an operation unit such as a touch button. However, the control computer 104, the display unit, and the operation unit may be included in, for example, a control box prepared separately from the base 105 and the support 106.

As illustrated in FIG. 10, the product B is continuously conveyed to the near-infrared inspection device 101 by the conveyors 111 and 112. The near-infrared inspection device 101 calculates the total number of objects contained as the product B thus conveyed. A calculation result of the total number is transmitted to a sorting mechanism (not illustrated) arranged downstream of the near-infrared inspection device 101. By the sorting mechanism, the product B having the calculation result of the total number within a predetermined range and the product B having a calculation result of the total number out of the predetermined range are sorted into a non-defective product and a defective product, respectively.

The control computer 104 includes a CPU 121, a ROM 122, a RAM 123, a USB 124 as an external connection terminal, and a high-capacity compact flash (CF) (registered trademark) 125. The CPU 121, the ROM 122, the RAM 123, the USB 124, and the CF 125 are mutually connected through an address bus and a data bus. The control computer 104 further includes a display control circuit that controls data display on a monitor 126, a key input circuit that receives key input data through a touch panel of the monitor 126, and an I/O port for performing, for example, control of data printing in a printer not illustrated.

The ROM 122 stores typical inspection programs for the mixed foreign substance inspection, the missing part inspection, and the crack inspection. The CF 125 stores various programs for inspecting the number of objects. The CF 125 stores therein, for example, the image processing program described later, the optimization program for optimizing the conversion table illustrated in FIG. 8 based on true masses, and the mass estimation program for estimating the mass of objects using the conversion table and calculating the number of objects from an estimated mass and a mass of one object. The CF 125 also stores the conversion table illustrated in FIG. 8, a true mass of one object, and the number of pixels occupied by one object in a near-infrared transmission image.

The control computer 104 is connected with, for example, a conveyor motor 112*f*, a rotary encoder 112*g*, the near-infrared emitter 113, the near-infrared line sensor 114, and a photoelectric sensor 115. The photoelectric sensor may not be provided, and a decrease in the luminance of an image detected by the line sensor may be recognized as passing of the product B.

Alternatively, the control computer 104 may receive the conveying speed of the conveyors 111 and 112 detected by the rotary encoder 112*g* mounted on the conveyor motor 112*f*, and receive a signal from the photoelectric sensor 115 as a synchronization sensor including a pair of a phototransmitter and a photoreceiver facing across any conveyor, thereby detecting a timing at which the product B as an inspection target reaches the position of the near-infrared line sensor 114.

Figure 11:
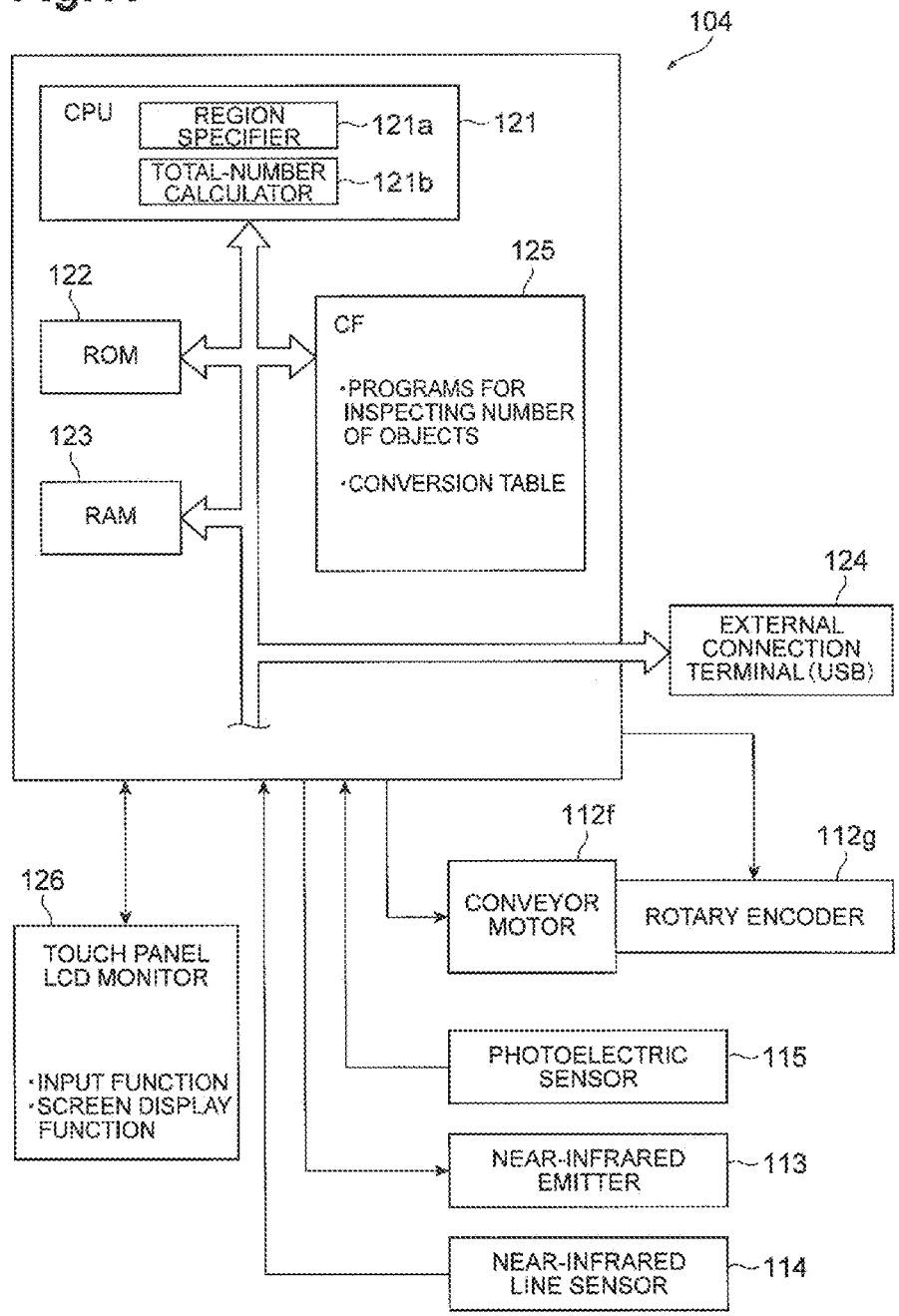
FIG. 11 is a block diagram of a functional configuration of the near-infrared inspection device of FIG. 10.

A region specifier 121a and a total-number calculator 121b illustrated in FIG. 11 represent functions achieved by the CPU 121 executing various programs. The CPU 121 reads out various programs front the ROM 122 and/or the CF 125 and executes, for example, the mixed foreign substance inspection, the missing part inspection, and the crack inspection. These inspections are not different from those conventional, and thus their descriptions are omitted. The inspection of the number of objects performed by the region specifier 121a and the total-number calculator 121b differs from that by the region specifier 11a and the total-number calculator 11b according to the first embodiment in that, whereas an X-ray transmission image is a target of image processing and image analysis by the region specifier 11a and the total-number calculator 11b, a near-infrared transmission image a target thereof by the region specifier 121a and the total-number calculator 121b. The specific contents of processing in both inspections are the same. Thus, a detailed description of the inspection by the region specifier 121a and the total-number calculator 121b are omitted.

In the above-described second embodiment, the present invention is explained with reference to the example in which inspection targets are a colorless or single color package and the product B having any object contained in the package has been explained, but the present invention is not limited thereto. For example, the package may have a plurality of colors. In this case, an acquired near-infrared image may be divided into regions by colors, and a filter may be set to each region. This allows color influence to be removed and the total mass of objects to be estimated. The package may have patterns thereon. In this case, applying image processing to the near-infrared image to remove the influence of the patterns enables the estimation of the total mass of objects.

The embodiments of the present invention are described above, but the present invention is not limited thereto and other embodiments are applicable. For example, in a case of a product in which a plurality of sausages are contained at random arrangement in a drawstring package, the total mass of the sausages contained in the drawstring package may be estimated based on the grayscale information on an X-ray transmission image or near-infrared image, and divided by a mass of one sausage to calculate the number of the sausages.

In a product such as a cookie box, when there are a plurality of lines of cookies aligned in a package, the number of cookies may be obtained for each line, and any defect may be determined for each line. In other words, one line may be treated as one object region to calculate the number of cookies for each line.

In the above-described embodiments, the present invention is explained with reference to the example of producing the table illustrated in FIG. 8 representing a relation between the grayscale level (brightness) of each pixel included in an X-ray transmission image or near-infrared transmission image and the estimated mass corresponding to the pixel, to estimate the mass of an object, but the present invention is not limited thereto. For example, the table as described above may not be produced for a part represented by an expression and the mass may be estimated using the expression. When an estimated mass is obtained using a table as in the embodiments, however, processing time needed to calculate the estimated mass can be markedly reduced as compared to a case of obtaining an estimated mass using an expression.

In the above-described embodiments, the present invention is explained with reference to the example of estimating the mass of contents based on the grayscale value of each pixel, but the present invention is not limited thereto. For example, a region having a predetermined number of pixels may be set as a unit region to estimate the mass of contents based on the grayscale value of the unit region.

In the above-described embodiments, the present invention is described with reference to the example of applying the present invention to the X-ray inspection device 1 or the near-infrared inspection device 101, but the present invention is not limited thereto. For example, the present invention is applicable to a program stored in the CF 14 of the X-ray inspection device 1 or a program stored in the CF 125 of the near-infrared inspection device 101 in the embodiments. In this case, the CPU 11 (121) may load the program to cause a computer to execute an X-ray inspection method (near-infrared inspection method) of performing processing in accordance with the flowchart illustrated in FIG. 9.

REFERENCE SIGNS LIST

1 . . . X-ray inspection device (inspection device), 4 . . . X-ray emitter, 5 . . . line sensor, 6 touch panel, 7 . . . controller, 11a, 121a . . . region specifier, 11b, 121b . . . total-number calculator, 101 . . . near-infrared inspection device (inspection device), 102 . . . light emitter, 103 . . . light detector, 104 . . . control computer 113 . . . near-infrared emitter, 114 . . . near-infrared line sensor, B . . . product

The invention claimed is:

1. An inspection device that emits light onto a product in which a plurality of objects each having a predetermined shape are contained, and inspects the number of the objects based on a transmission image obtained from light having transmitted through the product, the apparatus comprising:
   a region specifier configured to specify an object region, in which one or more objects are determined to exist, in the transmission image based on the number of pixels occupied by each object; and
   a total-number calculator configured to calculate a total number of the objects contained as the product, wherein
   for the object region in which the region specifier determines that two or more of the objects exist, the number of the objects included in the object region is specified by either or both of the region specifier and the total-number calculator, the region specifier separating the object region into regions for the respective objects based on the number of pixels occupied by each object, the total-number calculator estimating a total mass of the objects included in the object region based on grayscale information on part of the transmission image corresponding to the object region and dividing the total mass estimated by a mass per object, and
   the total-number calculator calculates, when the region specifier has specified that a plurality of the object regions exist based on distribution of the object regions in the transmission image, the total number of the objects contained in the product by summing the number of the objects in the object regions specified by either or both of the region specifier and the total-number calculator.

2. The inspection device according to claim 1, further comprising a storage configured to store the mass of one object, wherein
   when the region specifier has specified the object region in which only one of the objects is included, the total-number calculator estimates the mass of the objects based on grayscale information on the object region specified and updates the mass of one object stored in the storage with the mass estimated.

3. The inspection device according to claim 1, wherein for the object region in which the region specifier determines that two of the objects exist, the region specifier specifies the number of the objects included in the object region by separating the object region into regions for the respective objects based on the number of pixels occupied by each object, and for the object region in which the region specifier determines that three or more of the objects exist, the total-number calculator specifies the number of the objects included in the object region by estimating the total mass of the objects included in the object region based on grayscale information on part of the transmission image corresponding to the object region and dividing the total mass estimated by the mass per object.

4. The inspection device according to claim 2, wherein for the object region in which the region specifier determines that two of the objects exist, the region specifier specifies the number of the objects included in the object region by separating the object region into regions for the respective objects based on the number of pixels occupied by each object, and for the object region in which the region specifier determines that three or more of the objects exist, the total-number calculator specifies the number of the objects included in the object region by estimating the total mass of the objects included in the object region based on grayscale information on part of the transmission image corresponding to the object region and dividing the total mass estimated by the mass per object.

* * * * *